United States Patent
Klopp et al.

(10) Patent No.: US 7,074,953 B2
(45) Date of Patent: Jul. 11, 2006

(54) PRODUCTION OF AMMONIUM SALTS OF AROMATIC CARBOXYLIC ACIDS

(75) Inventors: Ingo Klopp, Weisenheim (DE); Thomas Bogenstätter, Bad Dürkheim (DE); Dirk Franke, Birkenheide (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/497,519

(22) PCT Filed: Dec. 3, 2002

(86) PCT No.: PCT/EP02/13678

§ 371 (c)(1),
(2), (4) Date: Jun. 3, 2004

(87) PCT Pub. No.: WO03/048099

PCT Pub. Date: Jun. 12, 2003

(65) Prior Publication Data

US 2005/0004393 A1    Jan. 6, 2005

(30) Foreign Application Priority Data

Dec. 4, 2001  (DE)  ............................. 101 59 420

(51) Int. Cl.
*C07C 63/00*   (2006.01)
(52) U.S. Cl. ............................... 562/405
(58) Field of Classification Search ........... 562/405, 562/400; 564/281, 282, 296
See application file for complete search history.

(56) References Cited

U.S. PATENT DOCUMENTS

| 2,220,692 | A |   | 11/1940 | Tabern et al. |
| 3,123,632 | A | * | 3/1964 | Katzschmann ............... 560/96 |
| 3,786,086 | A |   | 1/1974 | Skov et al. |
| 6,410,783 | B1 |  | 6/2002 | Peterson et al. ............ 562/405 |

FOREIGN PATENT DOCUMENTS

| GB | 1 296 442 |   | 11/1972 |
| JP | 01153654  | * | 6/1989 |
| WO | 9500469   | * | 1/1995 |

OTHER PUBLICATIONS

XP-002230602 Zhurnal Prikladnoi Khimii. vol. 63, No. 6, 1425-1428, Jun. 1990, Kozlov et al.

* cited by examiner

*Primary Examiner*—Johann Richter
*Assistant Examiner*—Karl Puttlitz
(74) *Attorney, Agent, or Firm*—Novak Druce Deluca & Quigg, LLP; Jason D. Voight

(57) ABSTRACT

A process is described for preparing ammonium salts of aromatic carboxylic acids by reacting an aromatic carboxylic acid with ammonia in an aprotic solvent, which comprises carrying out the reaction in a closed vessel by continuously introducing a solution of the aromatic carboxylic acid in the aprotic solvent and passing in gaseous ammonia so that an ammonia partial pressure in the range from 0.1 to 3 bar is maintained in the gas space of the vessel, and discharging a suspension of the ammonium salt in the aprotic solvent. The process allows the preparation of ammonium salts of defined crystal size having a narrow size distribution.

13 Claims, 1 Drawing Sheet

PRODUCTION OF AMMONIUM SALTS OF AROMATIC CARBOXYLIC ACIDS

TECHNICAL FIELD

Figure 1:
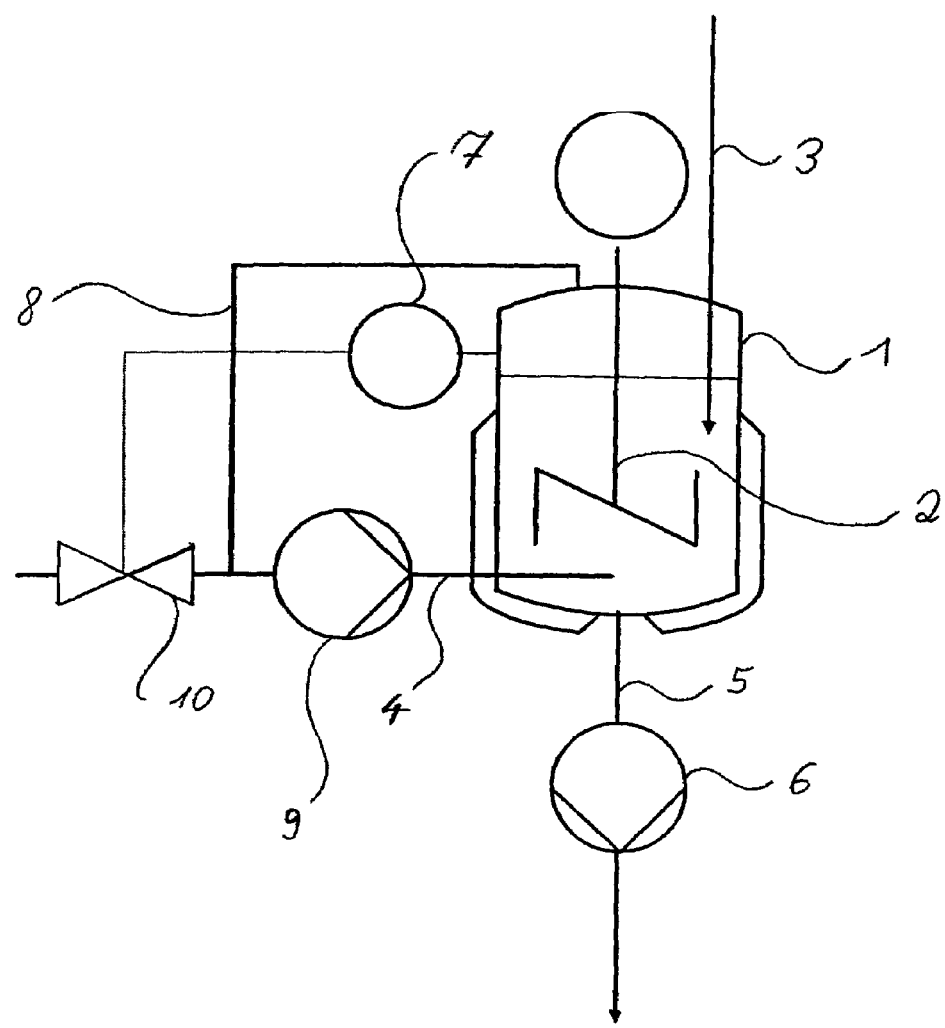

The present invention relates to a process for preparing ammonium salts of aromatic carboxylic acids, in particular of benzoic acid.

BACKGROUND ART

It is known that ammonium salts of aromatic carboxylic acids can be prepared by introducing gaseous ammonia into a solution of an aromatic carboxylic acid in an aprotic solvent. DE 1115729 describes such a process which employs dimethylformamide as solvent. U.S. Pat. No. 2,220,692 describes a process for preparing ammonium mandelate which involves treating a dispersion of mandelic acid in anhydrous benzene with ammonia. DE 2005514 describes a process for preparing thiolsulfinates by oxidizing the episulfides using an organic peracid, in particular perbenzoic acid, and precipitating the by-produced acid by introducing dry ammonia as the ammonium salt. The precipitation requires a low temperature of from −50 to −30° C.

Zh. Prikl. Khim. Vol.63, No. 6, p. 1425–1428 describes a process for preparing ammonium isobutyrate by reaction of isobutyric acid with ammonia in isopentane. The influence of the ammonia pressure is investigated, albeit only with respect to the initial formation rate of ammonium isobutyrate.

Although existing processes deliver crystalline ammonium salts, the crystal size distribution is wide and the crystal size not controllable. The achievable yields are unsatisfactory.

DISCLOSURE OF INVENTION

It is an object of the invention to provide a process for preparing ammonium salts of aromatic carboxylic acids which, when stoichiometric quantities of the reaction partners are used, leads in substantially quantitative yield to crystals of a defined size having a narrow size distribution.

We have found that this object is achieved by a process for preparing ammonium salts of aromatic carboxylic acids by reacting an aromatic carboxylic acid with ammonia in an aprotic solvent, which comprises carrying out the reaction in a closed vessel by continuously introducing a solution of the aromatic carboxylic acid in the aprotic solvent and passing in gaseous ammonia so that an ammonia partial pressure in the range from 0.1 to 3 bar is maintained in the gas space of the vessel, and discharging a suspension of the ammonium salt in the aprotic solvent.

MODE(S) FOR CARRYING OUT THE INVENTION

Useful aromatic carboxylic acids include those having at least one benzene ring and a carboxyl group which is bonded to the benzene ring either directly or via a $C_1$–$C_4$-alkylene chain. The benzene ring and alkylene chain may be unsubstituted or substituted by one to three substituents selected from $C_1$–$C_4$-alkyl, hydroxyl, $C_1$–$C_4$-alkoxy, halogen and nitro. Examples of useful aromatic carboxylic acids include 2-furancarboxylic acid, 3-furancarboxylic acid, 2-pyridinecarboxylic acid, 3-pyridinecarboxylic acid and 4-pyridinecarboxylic acid. The process according to the invention is particularly suitable for converting benzoic acid.

The solvent used according to the invention is aprotic (i.e. it has no acidic hydrogen atom). Useful aprotic solvents include aliphatic hydrocarbons, such as pentane, hexane, heptane, cyclohexane, methylcyclohexane or commercially available mixtures of aliphatic hydrocarbons, such as certain raffinate fractions; aromatic hydrocarbons, such as benzene, toluene, xylene or commercially available mixtures of aromatic hydrocarbons, for example Solvesso®150; halogenated aliphatic hydrocarbons, such as dichloromethane, trichloromethane, 1,2-dichloroethane, 1,2-dichloropropane, 1,1,2-trichloroethane, trichloroethylene; halogenated aromatic hydrocarbons, such as chlorobenzene; ethers, such as diethyl ether, ethylene glycol dimethyl ether, diethylene glycol dimethyl ether, diisopropyl ether, tetrahydrofuran, dioxane; ketones, such as acetone, methyl tert-butyl ketone, methyl isobutyl ketone or methyl ethyl ketone; dimethylformamide, dimethyl sulfoxide, sulfolane and aliphatic or aromatic nitriles, such as acetonitrile or benzonitrile. The solvents mentioned may be used individually or in the form of mixtures. Preference is given to 1,2-dichloroethane and 1,2-dichloropropane, and particular preference to 1,2-dichloroethane.

Useful reaction vessels for the process according to the invention include customary reactors which are preferably back-mixed, such as stirred reactors, loop reactors, stirred tank batteries and the like. The reaction vessel is preferably equipped with a stirring element, preferably one which allows a good distribution of the gas in the liquid, for example a disk stirrer or self-aspirating stirrer. The reaction vessel is charged with a solution of the aromatic carboxylic acid in the aprotic solvent. The solution may be passed in below or above the liquid surface of the reaction mixture present in the vessel.

Gaseous ammonia is passed into the reaction vessel so that an ammonia partial pressure in the range from 0.1 to 3 bar, preferably from 0.1 to 1 bar, is maintained in the gas space of the vessel. The ammonia partial pressure is conveniently determined as the difference of the overall pressure in the reaction vessel minus the system pressure, which is substantially determined by the vapor pressure of the solvent at the reaction temperature. The system pressure may be sufficiently accurately determined by introducing the chosen solvent into the reaction vessel, heating the reaction vessel to the reaction temperature and determining the pressure in the reaction vessel, which corresponds to the system pressure. If ammonia is introduced into the reaction vessel, the pressure increase relative to the system pressure corresponds to the ammonia partial pressure. If the process according to the invention is operated at constant temperature, a certain ammonia partial pressure can be maintained by monitoring the overall pressure in the reaction vessel and adding ammonia in such a way that the overall pressure remains constant. The pressure measurement and control of the ammonia introduction are preferably automated. The overall pressure (absolute pressure) is preferably from 1 to 7 bar, in particular from 1.1 to 6 bar.

The ammonia is preferably passed into the vessel below the liquid surface. Preference is given to continuously withdrawing gas from the gas space of the vessel, admixing it with fresh ammonia and passing it back into the vessel. This procedure allows an optimal ammonia conversion.

A suspension of the ammonia salt is discharged from the reaction vessel, preferably from the bottom. The discharge of the suspension is preferably effected continuously and preferably in such a way that the liquid level or the liquid quantity in the vessel remain constant. The discharged suspension may be fed directly or after passage through a heat exchanger to further reaction steps. The remaining content of aromatic carboxylic acid, which may be determined, for example, by means of high pressure liquid chromatography (HPLC), is typically less than 1000 ppm, mostly less than 200 ppm. If desired, the ammonium salt may be removed from the solvent by customary separating methods, for example filtration or centrifugation. The removed solvent may be fed back into the process.

The process according to the invention generally has a low concentration of ammonia and aromatic carboxylic acid in the liquid phase and accordingly low nucleation rates. This causes the aromatic carboxylic acid and the ammonia to react in the presence of previously formed crystals of the ammonium salt, which serve as seed crystals. The process according to the invention is therefore, in contrast to the prior art processes, not based on a spontaneous crystallization, which customarily leads to very wide crystal size distributions.

The temperature in the reaction vessel is preferably kept constant. The optimal reaction temperature is a function of the solubility of the ammonium salt in the solvent used. High temperatures increase the solubility of the ammonium salt and therefore support crystal growth, but also lead to stronger agglomerate formation and, during cooling, to precipitation of fine crystalline material. At low temperatures, the solubility of the ammonium salt is too low so that high supersaturations and accordingly only very fine crystals are formed. Preference is given to selecting the temperature in such a way that the solubility of the aromatic carboxylic acid in the solvent is more than 10 g/100 ml, in particular more than 35 g/100 ml, and the solubility of the ammonium salt is preferably less than 2 g/100 ml, in particular less than 1 g/100 ml. A temperature in the range from 70 to 110° C., preferably from 80 to 95° C., has, for example, proven to be suitable when the 1,2-dichloroethane is used as solvent.

The average residence time in the reaction vessel is preferably from 10 to 300 min. The lower limit of the average residence time is dictated by the mass transfer between gas and liquid, while a longer residence time makes the process uneconomical and leads to relatively wide crystal size distributions.

The process according to the invention allows a practically quantitative conversion of the aromatic carboxylic acid used. The crystals of the ammonium salt occur as a suspension in a solvent which is practically free of dissolved aromatic carboxylic acid. The suspension may be used in subsequent reactions without filtration or evaporation. The process allows the production of defined crystal sizes having narrow size distribution.

The invention is illustrated by the accompanying FIG. 1 and the following examples. The crystals obtained in the examples were examined using an optical microscope; the particle size distribution was determined by the method of laser extinction measurement by means of a particle counter (measurement range 2–400 µm; sensor 400 µm×400 µm). In each case, the maximum value and the range of the distribution (range=$(X_{90}-X_{10}/X_{50})$) are reported. To determine unconverted benzoic acid, the suspension was allowed to cool, the ammonium benzoate was filtered off and the filtrate analyzed by high pressure liquid chromatography.

FIG. 1 shows a plant suitable for operating the process according to the invention. The reactor 1, which is equipped with a stirring element 2, is charged via the pipe 3 with a solution of an aromatic carboxylic acid in an aprotic solvent. The pipe 4 is used to bubble in gaseous ammonia below the liquid surface. At the bottom of the reactor 1, a suspension of the formed ammonium salt is pumped off via the pipe 5 and the pump 6. From the gas space of the reactor 1, gas is withdrawn via the pipe 8 and the pump 9, admixed with fresh ammonia via the metering valve 10 and returned to the reactor 1 via pipe 4. The metering valve 10 is under the control of the pressure regulator 7.

INVENTIVE EXAMPLE 1

A 2 L double-jacketed reactor equipped with a disk stirrer and baffles was simultaneously charged below the liquid surface with 53.3 g min$^{-1}$ of a solution of 720 g of benzoic acid in 3280 g of 1,2-dichloroethane (DCE) and gaseous ammonia. The reaction temperature was 90° C., the overall pressure 1.6 bar and the ammonia partial pressure 0.38 bar. From the gas space, 50 l h$^{-1}$ of gas were circulated by pumping and introduced below the liquid surface. The residence time in the reactor was set to 45 minutes. The resulting ammonium benzoate suspension was continuously passed out through a bottom valve. After 8 residence times, a sample was analyzed: coarsely crystalline, non-agglomerated ammonium benzoate of an average particle size of about 300 µm (the particle size distribution could not be determined, since the particles clogged the sensor of the particle counter); dissolved benzoic acid: <10 ppm.

INVENTIVE EXAMPLE 2

The reactor described in example 1 was simultaneously charged below the liquid surface with 53.3 g min$^{-1}$ of a solution of 720 g of benzoic acid in 3280 g of DCE and gaseous ammonia. The reaction temperature was kept at 80 to 81° C., the overall pressure at 1.3 bar and the ammonia partial pressure at 0.37 bar. Unconverted ammonia was circulated as cycle gas via a pump at 60 l h$^{-1}$. The residence time in the reactor was set to 45 minutes. The resulting ammonium benzoate suspension was continuously passed out through the bottom valve. After 8 residence times, a sample was analyzed: coarsely crystalline, non-agglomerated ammonium benzoate; dissolved benzoic acid: <5 ppm; particle size distribution: maximum 90 µm, range 0.93.

INVENTIVE EXAMPLE 3

The reactor described in example 1 was simultaneously charged below the liquid surface with 53.3 g min$^{-1}$ of a solution of 720 g of benzoic acid in 3280 g of DCE and gaseous ammonia. The reaction temperature was set to 81° C., the overall pressure to 2.1 bar and the ammonia partial pressure to 1.19 bar. Unconverted ammonia was circulated as cycle gas via a pump at 60 l h$^{-1}$. The residence time in the reactor was set to 45 minutes. The resulting ammonium benzoate suspension was continuously passed out through the bottom valve. After 8 residence times, a sample was analyzed: finely crystalline, agglomerated ammonium benzoate; dissolved benzoic acid: 5 ppm; particle size distribution: maximum 60 µm, range 0.92.

COMPARATIVE EXAMPLE 1

The reactor described in example 1 was simultaneously charged below the liquid surface with 53.3 g min$^{-1}$ of a solution of 720 g of benzoic acid in 3280 g of DCE and 83.0 g h$^{-1}$ of gaseous ammonia. The reaction temperature was set to 8° C., and the overall pressure to 1.0 bar. The ammonia partial pressure was 0.07 bar. Unconverted ammonia was circulated as cycle gas via a pump at 50 l h$^{-1}$. The residence time in the reactor was set to 45 minutes. The resulting ammonium benzoate suspension was continuously passed out through the bottom valve. After 8 residence times, a sample was analyzed: finely crystalline, strongly agglomerated ammonium benzoate; dissolved benzoic acid: 1800 ppm; particle size distribution: maximum 290 µm, range 2.2.

COMPARATIVE EXAMPLE 2

A 2 L ground flange reactor equipped with a reflux cooler, stirrer and baffles was simultaneously charged below the liquid surface with 53.3 g min$^{-1}$ of a solution of 720 g of benzoic acid in 3280 g of 1,2-dichloroethane and 1.4 g min$^{-1}$ of gaseous ammonia. The reaction was conducted at atmospheric pressure. The temperature in the reactor was 80 to 82° C. Unconverted ammonia could escape through the reflux cooler. The ammonium benzoate suspension was continuously passed out through a bottom valve. The residence time was set to 45 min. After 6 residence times, a sample was withdrawn and analyzed: mixture of finely crystalline, strongly agglomerated ammonium benzoate with larger crystals; dissolved benzoic acid: 7200 ppm: particle size distribution: maximum 67 µm, range 1.24.

COMPARATIVE EXAMPLE 3

The reactor described in comparative example 2 was initially charged with 600 g of 1,2-dichloroethane and heated to reflux (about 84° C.). Then a solution of 558.2 g of benzoic acid in 2400 g of 1,2-dichloroethane and 85.6 g of gaseous NH$_3$ were simultaneously introduced over 45 minutes. The reaction temperature was from 81 to 82° C. The reaction was conducted at atmospheric pressure. Unconverted NH$_3$ escaped through the reflux cooler. After the metering in had ended, a sample was withdrawn from the reactor and analyzed: mixture of finely crystalline, strongly agglomerated ammonium benzoate (particle size <15 µm) and coarser crystals about 50 µm in size; dissolved benzoic acid: 50 ppm; particle size distribution: maximum 20 µm, range 1.53 (distribution was bimodal).

We claim:

1. A process for preparing an ammonium salt of an aromatic carboxylic acid by reacting the aromatic carboxylic acid with ammonia in an aprotic solvent, which comprises carrying out the reaction in a closed vessel comprising a gas space by continuously introducing a solution of the aromatic carboxylic acid in the aprotic solvent into the vessel and passing in gaseous ammonia so that an ammonia partial pressure in the range from 0.1 to 3 bar is maintained in the gas space of the vessel, and discharging a suspension of the ammonium salt of the aromatic carboxylic acid in the aprotic solvent, and wherein the aprotic solvent is selected from the group consisting of halogenated aliphatic hydrocarbons and halogenated aromatic hydrocarbons and mixtures thereof.

2. A process as claimed in claim 1, wherein the ammonia is passed into the vessel below the liquid surface of the reaction mixture.

3. A process as claimed in claim 2, wherein gas is continuously withdrawn from the gas space of the vessel, admixed with fresh ammonia and passed back into the vessel.

4. A process as claimed in claim 1, wherein the aprotic solvent is 1,2-dichloroethane or 1,2-dichloropropane.

5. A process as claimed in claim 1, wherein a temperature of from 70 to 110° C. is maintained in the vessel.

6. A process as claimed in claim 1, wherein an overall pressure of from 1 to 7 bar is maintained in the vessel.

7. A process as claimed in claim 1, wherein the average residence time in the vessel is from 10 to 300 min.

8. A process as claimed in claim 1, wherein the aromatic carboxylic acid is benzoic acid.

9. A process as claimed in claim 8, wherein the aprotic solvent is 1,2-dichloroethane or 1,2-dichloropropane.

10. A process as claimed in claim 1, wherein the ammonia partial pressure is maintained in the range from 0.1 to 1 bar.

11. A process as claimed in claim 10, wherein the aprotic solvent is 1,2-dichloroethane or 1,2-dichloropropane.

12. A process as claimed in claim 11, wherein the aromatic carboxylic acid is benzoic acid.

13. A process as claimed in claim 10, wherein the aromatic carboxylic acid is benzoic acid.

* * * * *